United States Patent [19]

Sakaguchi et al.

[11] Patent Number: 5,171,677
[45] Date of Patent: Dec. 15, 1992

[54] RECOMBINANT MAREK'S DISEASE VIRUS AND PROCESS FOR PREPARING THE SAME

[75] Inventors: Masashi Sakaguchi; Hiroaki Maeda; Michitaka Yamamoto; Junichi Miyazaki, all of Kumamoto, Japan

[73] Assignee: Juridical Foundation The Chemo-Sero-Therapeutic Research Institute, Kumamoto, Japan

[21] Appl. No.: 404,500

[22] Filed: Sep. 8, 1989

[30] Foreign Application Priority Data

Sep. 10, 1988 [JP] Japan .................................. 63-226960

[51] Int. Cl.⁵ ...................... C12N 15/64; C12N 15/86
[52] U.S. Cl. ................................ 435/172.3; 435/320.1
[58] Field of Search .................... 435/320.1, 172.3; 424/89

[56] References Cited

FOREIGN PATENT DOCUMENTS

| | | |
|---|---|---|
| 0334530 | 9/1989 | European Pat. Off. . |
| 87/04463 | 7/1987 | PCT Int'l Appl. . |
| 8700862 | 12/1987 | PCT Int'l Appl. . |
| 88/07088 | 9/1988 | PCT Int'l Appl. . |
| 89/01040 | 2/1989 | PCT Int'l Appl. . |

OTHER PUBLICATIONS

Hirai et al, J. of General Virology 45: 119–131 (1979).
Nevis Fregien et al., "Activating Elements in the Promoter Region of the Chicken β-actin Gene", Gene, vol. 48, pp. 1–11 (1986).
K. Fukuchi et al., "The Structure of Marek Disease Virus DNA: The Presence of Unique Expansion in Nonpathogenic Viral DNA", Proc. Natl. Acad. Sci., vol. 82, pp. 751–754, Feb. 1985.
Carol P. Gibbs et al., "Extensive Homology Exists Between Marek Disease Herpesvirus and its Vaccine Virus, Herpesvirus of Turkeys", Proc. Natl. Acad. Sci., vol. 81, pp. 3365–3369, Jun. 1984.
Chemical Abstracts, vol. 110, No. 17, Apr. 24, 1989, p. 231, Abstract No. 149170c.

Primary Examiner—Richard A. Schwartz
Assistant Examiner—S. L. Nolan
Attorney, Agent, or Firm—Wegner, Cantor, Mueller & Player

[57] ABSTRACT

A recombinant Marek's disease virus which comprises a Marek's disease virus genom and a DNA fragment incorporated therein, said DNA fragment being constructed by incorporating a promoter derived from an animal cell or an animal virus and a structural gene coding for an exogenous protein into a gene fragment derived from a Marek's disease virus, a process for preparing the same which comprises preparing a gene fragment wherein a structural gene coding for an exogenous gene is linked to the downstream of a promoter derived from an animal cell or an animal virus, incorporating said gene fragment into a BamHI - H fragment of a gene of a Marek's disease virus type I, and incorporating said fragment into a Marek's disease virus type I genome, and a multivalent live vaccine for birds comprising the same.

5 Claims, 2 Drawing Sheets

RECOMBINANT MAREK'S DISEASE VIRUS AND PROCESS FOR PREPARING THE SAME

The present invention relates to a novel recombinant Marek's disease virus which enables an expression of an exogenous gene product in a chick cell or in a body of a chick and a process for preparing the same. The present invention further relates to a multivalent live vaccine comprising said recombinant Marek's disease virus.

TECHNICAL BACKGROUND AND PRIOR ART

In the field of modern poultry farming, prevention of diseases by vaccination is a major means for sanitation regardless of the kind of chicks, being raised i.e. a chick for breeding, a chick for laying eggs or a chick for meat. The vaccination, however, has to be done so frequently that personnel expenses become much higher, causing an economical disadvantage for a poultry farmer. In order to avoid this disadvantage, one can contemplate simply mixing several known vaccines. However, there is a problem of interference occuring between viruses in the case of a mixture of live vaccines and there is also a limitation in the mixing amount in the case of a mixture of inactivated vaccines. In addition, in the case of a mixture of a live vaccine and an inactivated vaccine, a titer decrease is observed due to an adsorption of a live vaccine antigen to a gel (adjuvant).

Recently, taking into account the above situations, alternative method has been attempted to employ a virus vector, i.e. multiple genes of vaccine antigenes are incorporated into a single virus to prepare a multivalent live vaccine. This method makes it possible to prepare a multivalent live vaccine without causing the interference between viruses or the increase of inoculation amount in case of the mixture of inactivated vaccines as mentioned above.

Hitherto, a research has already been conducted to use a virus as a vector in various viruses such as vaccinia virus, adenovirus, herpes simplex virus, retrovirus, and the like, and HBs antigen (Hepatitis B surface antigen) or glycoproteins of rabies virus or herpes zoster virus have successfully been expressed in vitro. However, these viruses other than vaccinia virus are a virus having an oncogencity and hence the administration of these viruses to human or animals is restricted and not practical from the viewpoint of safety. As to vaccinia virus, although the virus itself is safe, it cannot be used effectively as a virus vector for birds, at which the present invention is aimed, since the birds to be inoculated are not an original host of the vaccinia virus. For the same reason, the other viruses as mentioned above cannot be used effectively as a virus vector for birds.

Use of avian poxvirus (e.g. chick fowlpox virus) as a vector also has been suggested and the virus has already been studied for use as a virus vector. It is reported that an exogenous gene can be incorporated into the virus DNA [Saeki et al., Abstract of the 35th Meeting of Japan Virology Society, page 209 (1987)].

However, in the modern poultry field, immunity against fowlpox lasts for only short period of time, and hence, several inoculations of a vaccine virus (attenuated fowlpox virus or ornithosis virus) are usually required during the breeding of chick. Consequently, when the poxvirus is used as the virus vector, a frequent vaccination is still required even though a virus vector wherein plural antigens are incorporated is prepared and used as a vaccine.

BRIEF SUMMARY OF THE INVENTION

Under such circumstances, the present inventors have intensively studied to develop a virus vector by utilizing a virus with a long immune period of time and an avian host, and as a result, have found that an exogenous gene can effectively be incorporated into Marek's disease virus and that the recombinant Marek's disease virus thus obtained can be used as the virus vector.

That is, the present invention provides a novel recombinant Marek's disease virus useful for an avian vaccine, a process for preparing said virus and a multivalent live vaccine for birds comprising said recombinant Marek's disease virus.

DETAILED EXPLANATION OF THE INVENTION

Figure 1:
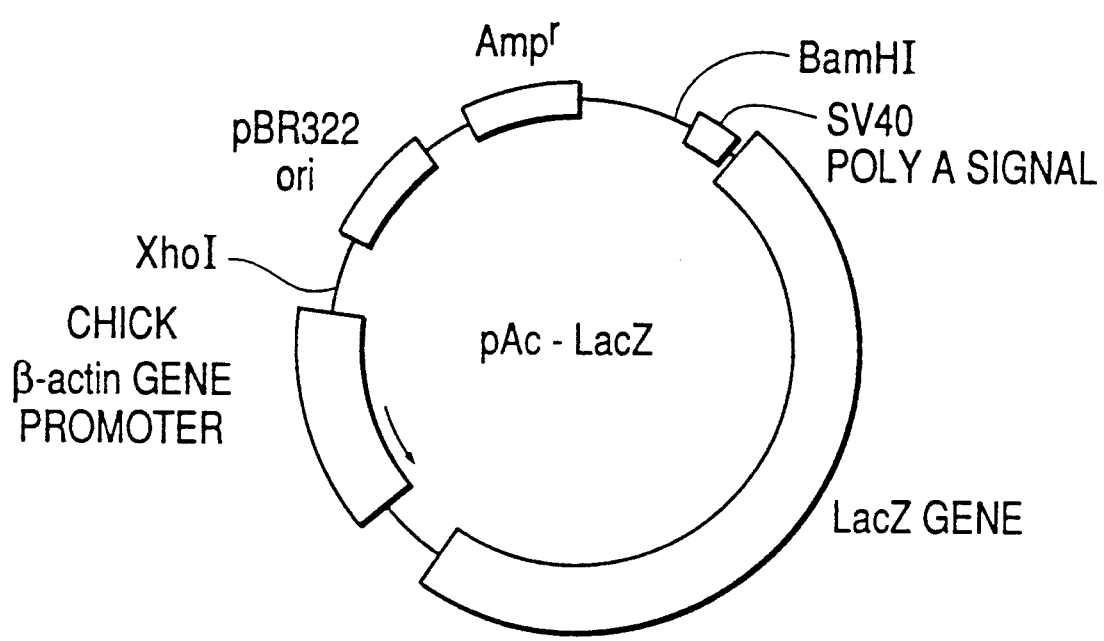
FIG. 1 shows the structure of plasmid pAc-LacZ wherein a LacZ gene is incorporated into the downstream of a chick $\beta$-actin gene promoter.

Marek's disease is a malignant tumor whose outbreak can be prevented only by vaccination. The prevention mechanism is considered to be that when the host bird such as a chick is permanently infected with the vaccine virus humoral, cell-mediated immunities against Marek's disease virus are induced and maintained through the life of the host, and thereby tumorigenesis by virulent virus is suppressed. Accordingly, when an exogenous gene coding for a vaccine antigen for other diseases is incorporated into Marek's disease virus and the recombinant virus is inoculated to birds, the antigen derived from the exogenous gene keeps on being expressed for a long period of time or even through the life of the host birds by the same mechanism as Marek's disease virus, thereby causing humoral or cell-mediated immunity against said antigen for a long period of time or even through the life of the host. That is, in accordance with the present invention, a multivalent live vaccine can be prepared which can afford immunity against a number of pathogens only by a single administration to birds such as chicks when hatched.

As a vaccine against Marek's disease, there have hitherto been known those comprising an attenuated Marek's disease virus type I (MDV-I), herpes virus of turkey (HVT: MDV-III) or a mixture of Marek's disease virus type II and herpes virus of turkey.

Since the restriction enzyme pattern of the virus genome DNA has been partly made clear, these viruses belonging to each serotype (I to III type) can be distinguished from each other in a comparatively easy manner by analyzing the virus genome (Archives of Virology 89, 113-130, 1986). It is also known that these viruses have homology in DNA of only 5% or less (Advances in Virus Research, Vol. 30, 225-227).

Since it has been found that Marek's disease itself is induced by the infection of type I virus, it is preferable to use an attenuated vaccine of the serologically homologous virus, i.e. Marek's disease virus type I, for prevention of outbreak of the disease. In the preferred embodiment of the present invention, accordingly, Marek's disease virus type I is used for preparing the recombinant Marek's disease virus of the present invention which is useful as a multivalent vaccine including Marek's disease vaccine.

In order to prepare the multivalent live vaccine of the present invention in which Marek's disease virus, the virus having much more excellent properties than those of other virus vectors, is utilized as a vector, it is necessary to find out the site suitable for incorporation of an exogenous gene or the removable region on the Marek's disease virus DNA.

However, the Marek's disease virus DNA has not yet been analyzed, unlike poxvirus or adenovirus, and there is merely known a mapping with only two or three restriction enzymes [Kunihiko Fukuchi et al., J. Virol., 51, 102 (1984)]. Further, as a region coding for a specific protein, only one region has been known, i.e. a BamHI - B fragment which is prepared by digesting the Marek's disease virus gene with restriction enzyme BamHI and which codes for gA [R. J. ISFORT et al., J. Gen. Virol., 61, 2614 (1987)], and the remainder of the gene has not yet been analyzed.

Like gB, gA is one of major glycoproteins produced by the virus. Although it is known that inoculation of gB induces the production of a neutralizing antibody in animal body, it has not yet been observed by inoculation of gA, nevertheless, it is expected that gA causes cellular immunization. Therefore, if the Marek's disease virus is desired to have both functions as a vector and as a vaccine, the insertion of an exogenous gene into this gA gene to mutate the gA gene is undesirable since this will deteriorate the function as a vaccine. A gene which is not indispensable for viral growth includes a TK gene. In case of herpes virus, the TK gene has been used as an insertion region of an exogenous gene. It is estimated that the Marek's disease virus type I also contains this TK gene, but it is reported that the deletion of the TK gene generally reduces viral growth (12th INTERNATIONAL HERPES VIRUS WORKSHOP, page 68, 1987), and hence, the insertion of an exogenous gene into the TK gene is also undesirable when taking into account the function as a vaccine.

Under the circumstances, the present inventors have intensively studied as to less analyzed gene in order to prepare an effective recombinant Marek's disease virus, and as a result, have found that the recombinant Marek's disease virus can be obtained by using a BamHI - H fragment of the Marek's disease virus type I gene (the 8th fragment from the biggest prepared by digesting the Marek's disease virus gene with restriction enzyme BamHI).

According to the present invention, the recombinant Marek's disease virus can be prepared without losing the major antigenicity as necessary for the Marek's disease vaccine such as gA and gB. That is, the recombinant Marek's disease virus prepared according to the present invention, which includes the insertion of one or more exogenous genes coding for antigens effective as a vaccine for diseases other than Marek's disease, can be made into an extremely excellent multivalent live vaccine comprising the virus which can effectively express the desired exogenous genes without reducing the function as the Marek's disease vaccine.

Thus, it has unexpectedly been found by the present inventors that the Marek's disease virus can be used as the recombinant virus vector, while it has hitherto never been used for such a purpose; that there is a region in the virus DNA where an exogenous gene can be incorporated; and that the recombinant virus wherein said exogenous gene is incorporated into said region can multiply and express the exogenous gene product.

The preparation of the recombinant Marek's disease virus of the present invention is described in more detail hereinbelow.

Generally, the preparation of the recombinant virus of the present invention is carried out by the following procedures:

(i) A part of viral DNA is cloned into a vector.

(ii) A DNA fragment is constructed wherein a gene fragment enabling an expression of a desired exogenous gene (expression operon) is incorporated into said cloned viral DNA fragment.

(iii) Said DNA fragment is transduced into virus-infected cells.

(iv) A recombinant virus containing the exogenous gene is selected by a suitable method.

In the present invention, the recombination procedure has been conducted using various gene fragments from the Marek's disease virus type I gene and then the obtained recombinant viruses have been cloned. As a result, it has been found that a BamHI - H fragment is most preferable for the gene fragment derived from the virus which is used for incorporation of the exogenous gene into the Marek's disease viral genom.

The gene fragment used for incorporation of the exogenous gene may be either a circular DNA (plasmid) or a linear DNA. The fragment basically contains a structure which is constructed by incorporating a promoter derived from an animal cell or an animal virus and a structural gene coding for a desired exogenous protein into a gene fragment derived from a Marek's disease virus. By employing such recombinant gene fragment, the desired expression gene is incorporated into the virus genom at the site having a homology with the gene fragment derived from the virus. In case of the transduction of the virus with the plasmid, the plasmid may previously be digested with a suitable restriction enzyme to be linearized and the virus may be transduced with this linearized plasmid.

In the above procedure (i), the viral DNA is firstly digested with a restriction enzyme and then the digested products are subjected to an agarose gel electrophoresis to separate fragments from each other and to collect fragments from the gel. Each of the obtained fragments is cloned into a plasmid. The cloning vector used therein includes cosmid, phage etc.

In the procedure (ii), each viral fragment cloned into the plasmid in the above procedure (i) is digested with an appropriate restriction enzyme at one site or at two sites to delete a part of the viral fragment and thereto are incorporated a promoter capable of functioning in an animal cell and a structural gene coding for a desired exogenous protein at the downstream of said promoter.

The promoter used for expression of the exogenous gene includes a promoter derived from an animal cell or an animal virus, most preferably a chick $\beta$-actin gene promoter. The chick $\beta$-actin gene promoter shows an extremely higher promoter activity than the conventional well-known SV40 early gene promoter (Jun-ichi Miyazaki et al., Japanese Patent Application No. 157569/1988). The recombinant virus prepared according to the present invention using the chick $\beta$-actin gene promoter with a powerful promoter activity is capable of expressing a variety of desired vaccine antigens at a high degree.

Furthermore, a plural of a desired expression gene fragment (i.e. a gene fragment comprising a promoter and an exogenous structural gene) can be incorporated into said DNA fragment derived from virus so that the recombinant virus of the present invention can express a plural of exogenous antigen. The recombinant Marek's disease virus thus obtained provides an extremely excellent multivalent vaccine.

The procedure (iii) is a homologous recombination of viral DNA fragment including an exogenous gene into a viral DNA and can be conducted by either introducing the above plasmid into the virus-infected cell, or alternatively, by simultaneously introducing the viral DNA and the plasmid. The transduction can be conducted by any known process such as a calcium phosphate method, a DEAE-dextran method, or an electroporation.

The selection of the recombinant virus containing the desired exogenous gene in the procedure (iv) can be carried out by using a suitable means selected depending on a kind of the exogenous gene to be incorporated into the viral DNA. For example, as shown in the following Example, in case of the selection of a recombinant virus wherein a gene coding for $\beta$-galactosidase ($\beta$-gal)(which is referred to as "LacZ gene") is incorporated into the Marek's disease virus for expressing $\beta$-galactosidase, a substrate of $\beta$-galactosidase [e.g. X-Gal (5-bromo-4-chloro-3-indolyl $\beta$-D-galactopyranoside)] is added to an agar-overlayed cell sheet, by which a plaque of virus showing $\beta$-galactosidase activity can be distinguished by color [S. CHAKRABBARTI et al., Mol. Cell. Biol., 5, 3403 (1985); Saeki et al., Abstract of the 35th Meeting of Japan Virology Society (1987)].

The thus obtained recombinant Marek's disease virus of the present invention is very useful for a multivalent live vaccine for birds, particularly for chicks. That is, the recombinant Marek's disease virus of the present invention wherein an exogenous gene capable of expressing a vaccine antigen against infectious diseases other than Marek's disease is incorporated is quite useful as a multivalent live vaccine showing an immune prolonging effect inherent in Marek's disease virus.

The present invention is more specifically illustrated by the following Examples but should not be construed to be limited thereto.

EXAMPLE 1

Isolation of Marek's Disease Virus DNA - BamHI - H Fragment

After inoculating Marek's disease type I virus into chick embryo fibroblasts (hereinafter referred to as "CEF"), the virus-infected cells were harvested at the time when cytopathic effect (CPE) was strongly shown and the viral DNA was purified according to the method of Hirai et al., [J. Gen. Virol., 45, 119 (1979)].

That is, the virus-infected cells were collected by centrifugation and thereto was added a double amount of a 1% NP40 solution (0.01M Tris-HCl, pH 7.4, 0.01M NaCl, 0.0015M MgCl$_2$) and the mixture was ice-cooled for 30 minutes and then pipetted. After the solution was centrifuged at 2,500 rpm for 10 minutes, the supernatant was overlayed on a 40%–60% (w/w) sucrose solution (0.02M Tris-HCl, pH 7.4, 0.15M NaCl). After centrifugation at 175 KG for 2 hours, a layer containing a capsid derived from the Marek's disease virus, the layer being formed between the 40% sucrose solution and the 60% sucrose solution, was separated. This intermediate layer was resuspended in a solution containing 0.02M Tris-HCl, pH 7.4 and 0.15M NaCl and the suspension was centrifuged at 160 KG for 1 hour and pelleted. The obtained pellet was suspended in a 1% SDS solution (0.1% Tris-HCl, pH 7.4, 0.01M EDTA, 1% Sarcosinate; Nakarai Kagaku Co. Ltd.,) supplemented with Proteinase K (0.1%; Boehringer Mannheim) and the suspension was left to stand at 37° C. overnight. Then DNA was collected by a phenol treatment and an ethanol precipitation. The obtained DNA was dissolved in a TE buffer (10 mM Tris-HCl, pH 7.4, 1 mM EDTA) and the solution was overlayed on a 10%–30% glycerol gradient solution, followed by centrifugation at 175 KG for 4 hours. Then the solution was fractionated from the bottom of the centrifuge tube and a fraction containing the viral DNA was separated. An equivalent amount of a 10% trichloroacetic acid was added to the viral DNA-containing fraction to precipitate DNA and the precipitated DNA was collected.

Then, the above purified DNA (10 µg) was digested with restriction enzyme BamHI (Takara Shuzo Co. Ltd.,; the reagents used in the following Examples are manufactured by Takara Shuzo Co. Ltd., or Toyobo Co. Ltd., unless otherwise mentioned) and the obtained fragments were subjected to a 0.5% agarose gel electrophoresis to separate from each other. After a fraction containing an H fragment was eluted from the gel by an electroelution procedure, the fragment was collected by a phenol treatment and an ethanol precipitation. The thus obtained fragment (about 40 ng) was ligated to pUC19 plasmid (20 ng) with T4 DNA ligase. E. coli competent cells were transduced with the ligate and the transduced cells were spread over an agar plate containing ampicillin and X-Gal. White colonies which did not produce $\beta$-gal due to transfection were collected and cultured on an LB medium supplemented with ampicillin (100 µg/ml). Plasmids within cells were collected by the conventional alkali procedure and digested with a restriction enzyme BamHI to select a transformant containing a plasmid wherein the BamHI - H fragment was inserted.

Figure 2:
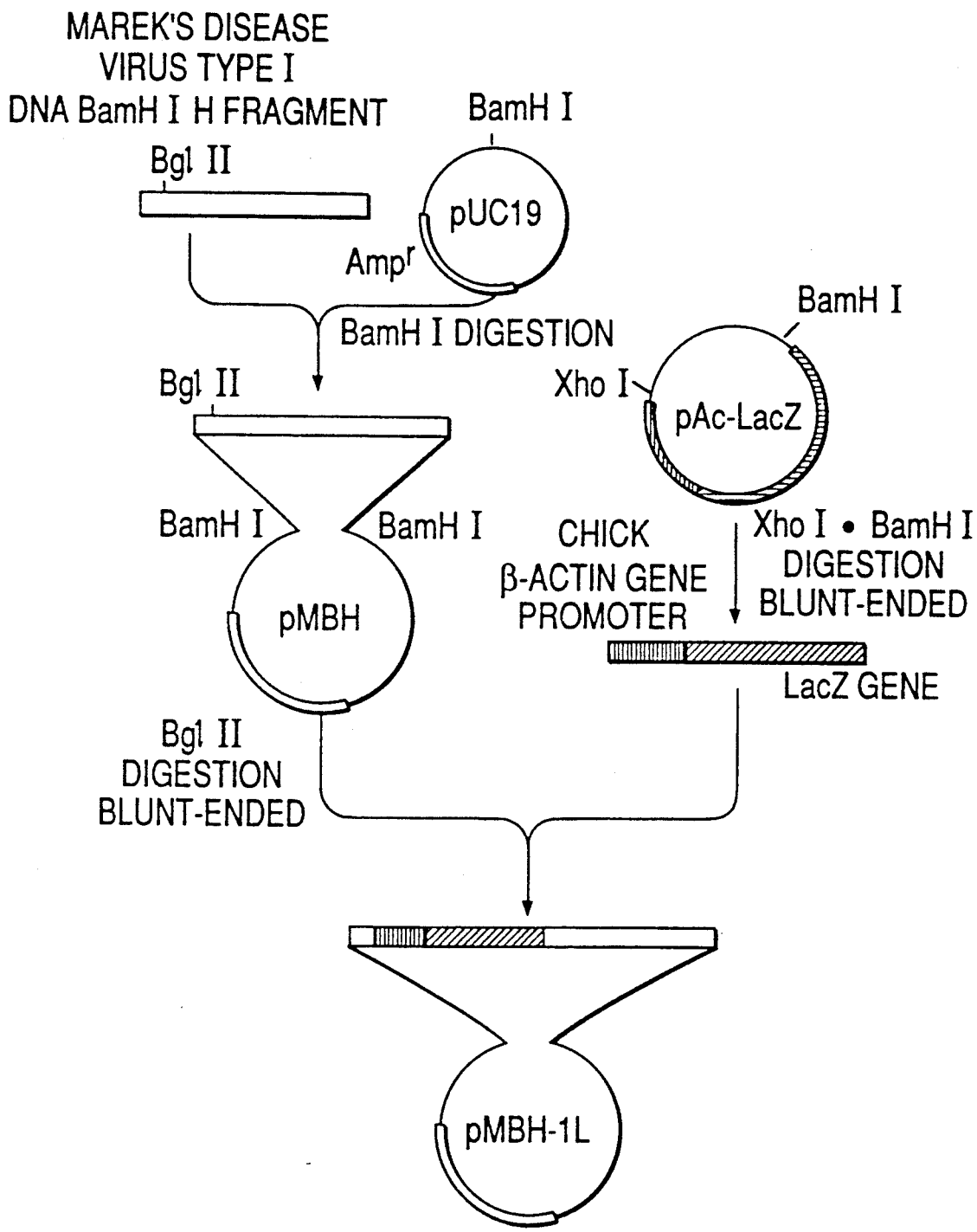
FIG. 2 shows the construction of plasmid pMBH wherein a BamHI - H fragment of Marek's disease virus type I DNA is incorporated and of plasmid pMBH-1L wherein a chick $\beta$-actin gene promoter and a LacZ gene are incoporated as well as a BamHI - H fragment of Marek's disease virus type I DNA.

The thus obtained plasmid was referred to as "pMBH" (see FIG. 2).

EXAMPLE 2

Construction of Plasmid "pMBH-lL" which Contains H Fragment with Inserted LacZ Gene The plasmid pMBH was digested with a restriction enzyme BglII and the 5' end thereof was dephosphorylated with alkaliphosphatase derived from E. coli (BAP).

Then, a NcoI fragment of a plasmid pAZ1037 containing the first exon, the first intron and a part of the second intron of a chick $\beta$-actin gene and a CAT gene adjacent thereto [NATURE, 314, 286–289 (1985)] was treated with a modification enzyme S1 nuclease to delete the chick $\beta$-actin structural gene [3' site from ATG (initiation codon)] at the downstream of the chick $\beta$-actin gene promoter, and thereto a HindIII linker was linked. The resultant was treated with restriction enzymes HindIII and BamHI to give a gene fragment containing the chick $\beta$-actin gene promoter. On the other hand, a plasmid pCH110 containing a whole lacZ gene (Pharmacia) was digested with restriction enzymes HindIII and BamHI to give a gene fragment of about 3.8 kbp. The thus obtained two HindIII-BamHI fragments were linked to each other to cyclize to give a plasmid pAc-lacZ wherein the lac gene was incorporated at the downstream of the chick β-actin gene promoter (FIG. 1). The plasmid pAc-lacZ was treated with restriction enzymes BamHI and XhoI and the obtained fragments were separated from each other by 0.8% gel electrophoresis. A fragment of about 5.2 kbp was collected, blunt-ended and a 40 ng portion thereof was then linked to the above linearized pMBH (20 ng) with T4 DNA ligase and the ligate was introduced into HB101. After the transformed HB101 was spread over an agar plate containing ampicillin (100 μg/ml) and cultured at 37° C., six transformed colonies resistant to ampicillin were selected and cultured in an LB medium containing ampicillin (100 μg/ml). After the plasmids were isolated, they were analyzed for a digestion pattern with restriction enzymes BamHI and HindIII. One plasmid which showed an expected digestion pattern in a 0.8% agarose gel electrophoresis was designated as "pMBH-lL" (FIG. 2).

EXAMPLE 3

Preparation of Marek's Disease Virus Containing LacZ Gene

Primary CEFs cultured at 37° C. overnight were harvested and washed with an EDTA-trypsin solution and then suspended in an Eagle-MEM (E-MEM; Nissui Co. Ltd.,) medium supplemented with a 5% bovine serum (hereinafter referred to as "BS") at a cell concentration of $2\times10^5$ cells/ml. Forty milliliters of the suspension was put in a tissue culture flask manufactured by Falcon (No. 3028) and cultured at 37° C. for 16 hours. A sheet rate of the cell at this point was about 50%. Marek's disease type I virus-infected CEFs (about $8\times10^5$ cells) were inoculated thereto and cultured at 37° C. for 4 hours. The cells were again harvested with an EDTA-trypsin solution and washed once with the E-MEM supplemented with a 5% BS and then twice with a phosphate buffer supplemented with sucrose (sucrose 272 mM, potassium phosphate 7 mM, $MgCl_2$ 1 mM, pH 7.4). Finally, the cells were suspended in the phosphate buffer supplemented with sucrose (0.7 ml) and the suspension was put in a cuvette for electroporation (Bio-Rad, No. 165-2085). The suspension was added with pMBH-lL (40 μg) and ice-cooled for 10 minutes. Then, the electroporation was conducted in accordance with a manual attached to a gene pulser manufactured by Bio-Rad under the condition of 200 V–25 μF and one pulse. After ice-cooling for additional 10 minutes, the resultant was mixed with primary CEFs which were cultured on the previous day and harvested and the mixture was suspended in the E-MEM supplemented with a 5% BS (Nissui Co. Ltd.,) at a final concentration of $2\times10^6$ cells/ml. Each 13 ml of the suspension was poured into 10 Petri dishes (diameter: 10 cm, manufactured by Falcon, No. 3003) and the culture was conducted at 37° C. After 2 to 3 days, the cells were harvested with the EDTA-trypsin solution and subcultured onto a CEF cell sheet cultured overnight. Thereto was overlayed a phenol red-deficient E-MEM supplemented with a 1% BS which was supplemented with a 1% agarose and the culture was further continued at 37° C. for several days. Thereto a 1% agarose/E-MEM (defective of phenol red) containing chlorophenol red β-D-galactopyranoside (Seikagaku Kogyo Co. Ltd., 100 μg/ml) was then overlayed and the resultant was left to stand at 37° C. for several hours.

As a result, red virus plaques having β-gal activity was observed at a rate of 10 to 30 plaques per Petri dish. These red plaques were not observed when only pMBH-lL was introduced into the cell by electroporation or only the virus was treated in the same manner. When these red plaques were cloned and inoculated into CEFs of the second generation which were cultured on the previous day, these plaques were subcultured and showed the same red plaques due to β-gal by the same procedure as described above, which means that a stable incorporation of the plasmid into the virus could be effected.

The thus obtained recombinant Marek's disease virus of the present invention was studied for its messenger RNA and it was confirmed that both mRNAs of the gA and gB antigens, both of which were necessary for preparing the Marek's disease vaccine, were translated in the virus-infected cells as before the gene recombination.

What is claimed is:

1. A process for preparing a recombinant Marek's disease virus which comprises preparing a gene fragment wherein a structural gene coding for an exogenous gene is linked to the downstream of a promoter derived from an animal cell or an animal virus, and incorporating said gene fragment into a BamHI - H region of a Marek's disease virus type I genome.

2. The process of claim 1 wherein said promoter is a β-actin gene promoter derived from a chicken.

3. The process of claim 1 wherein the gene fragment wherein the structural gene coding for the exogenous gene is linked to the downstream of the promoter derived from the animal cell or the animal virus is incorporated into a BglII site of the BamHI - H fragment.

4. A recombinant Marek's disease virus type I which comprises an insertion of heterologous DNA wherein said heterologous DNA is inserted into the BamHI-H fragment of said virus and wherein said heterologous DNA comprises a promoter from an animal cell or animal virus operably linked to a structural gene coding for an exogenous protein.

5. The recombinant Marek's disease virus of claim 4 wherein said promoter is a β-actin gene promoter derived from a chicken.

* * * * *